United States Patent
Neuba et al.

(10) Patent No.: US 9,918,928 B2
(45) Date of Patent: *Mar. 20, 2018

(54) MULTI-TONAL ONE STEP DYEING WITH THICKENING PRE-TREATMENT SOLUTION

(71) Applicant: Henkel AG & Co. KGaA, Duesseldorf (DE)

(72) Inventors: Constanze Neuba, Grevenbroich (DE); Burkhard Mueller, Duesseldorf (DE)

(73) Assignee: Henkel AG & CO. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,166

(22) Filed: Feb. 16, 2017

(65) Prior Publication Data
US 2017/0157023 A1   Jun. 8, 2017

Related U.S. Application Data

(63) Continuation of application No. PCT/EP2015/068563, filed on Aug. 12, 2015.

(30) Foreign Application Priority Data

Aug. 26, 2014   (DE) .......... 10 2014 216 942

(51) Int. Cl.
| | | |
|---|---|---|
| *A61Q 5/10* | (2006.01) | |
| *A61K 8/81* | (2006.01) | |
| *A61K 8/73* | (2006.01) | |
| *A61K 8/22* | (2006.01) | |
| *A61K 8/49* | (2006.01) | |
| *A61K 8/42* | (2006.01) | |
| *A61K 8/23* | (2006.01) | |
| *A61K 8/20* | (2006.01) | |
| *A61K 8/19* | (2006.01) | |

(52) U.S. Cl.
CPC .............. *A61K 8/8182* (2013.01); *A61K 8/19* (2013.01); *A61K 8/20* (2013.01); *A61K 8/22* (2013.01); *A61K 8/23* (2013.01); *A61K 8/42* (2013.01); *A61K 8/4966* (2013.01); *A61K 8/73* (2013.01); *A61K 8/731* (2013.01); *A61K 8/8147* (2013.01); *A61K 8/8152* (2013.01); *A61K 8/8158* (2013.01); *A61Q 5/10* (2013.01); *A61K 2800/4324* (2013.01); *A61K 2800/884* (2013.01)

(58) Field of Classification Search
CPC .... A61K 8/8182; A61K 8/731; A61K 8/8147; A61K 8/8152; A61K 8/22; A61K 8/73; A61K 8/4966; A61K 8/42; A61K 8/23; A61K 8/19; A61K 2800/4324; A61K 2800/884; A61Q 5/10
See application file for complete search history.

(56) References Cited

U.S. PATENT DOCUMENTS

| | | | |
|---|---|---|---|
| 4,370,142 A | 1/1983 | Bugaut et al. | |
| 4,425,132 A | 1/1984 | Grollier et al. | |
| 6,916,343 B1 * | 7/2005 | Akram | ............. A61K 8/418 8/405 |
| 9,402,795 B2 * | 8/2016 | Neuba | ............. A61Q 5/10 |
| 9,402,797 B2 * | 8/2016 | Neuba | ............. A61Q 5/10 |
| 9,445,977 B2 * | 9/2016 | Neuba | ............. A61K 8/411 |
| 2005/0000035 A1 * | 1/2005 | Chan | ............. A61K 8/22 8/405 |

FOREIGN PATENT DOCUMENTS

| | | |
|---|---|---|
| DE | 20100140 U1 | 6/2002 |
| WO | 03/068177 A2 | 8/2003 |

OTHER PUBLICATIONS

Foreign application No. 10 2014 216 942.9 filed on Aug. 26, 2014.*
PCT International Search Report (PCT/EP2015/068563) dated Jul. 9, 2015.

* cited by examiner

*Primary Examiner* — Eisa B Elhilo
(74) *Attorney, Agent, or Firm* — David K. Benson

(57) ABSTRACT

A method for dyeing keratin fibers, in particular human hair, in which, after a thickened pretreatment agent (M1) including at least one oxidation dye precursor has been applied and left to act, directly thereafter and without rinsing a coloring agent (M2) is applied and left to act. By virtue of this method, in one dyeing step the hair can be colored and at the same time a multi-tonal dyeing with lighter ("highlights") or darker ("lowlights") sections (strands) can be produced.

16 Claims, No Drawings

MULTI-TONAL ONE STEP DYEING WITH THICKENING PRE-TREATMENT SOLUTION

FIELD OF THE INVENTION

The present invention is a method for treating keratin fibers, which makes it possible in one dyeing step to color the hair and at the same time produce a multi-tonal dyeing with lighter ("highlights") or darker ("lowlights") sections (strands).

BACKGROUND OF THE INVENTION

Hair loses or changes its natural color and its gloss or shine over time and in particular under the effect of external influences such as light or atmospheric pollutants. For this reason, hair coloring agents are widely used, these being used either in hairdressing salons or at home.

For permanent, intense colorations with suitable fastness properties, use is made of so-called oxidation coloring agents. Such coloring agents usually contain oxidation dye precursors, so-called developer components and coupler components, which together form the actual dyes under the effect of oxidizing agents or atmospheric oxygen. Oxidation coloring agents are characterized by excellent, long-lasting color results. For temporary colorations, use is usually made of coloring or toning agents which contain so-called substantive dyes as the coloring component.

Besides dyeing, many consumers also have the very specific desire to lighten their own hair color or to become blonde, since a blonde hair color is considered to be attractive and fashionable. If substrates are to be lightened or even bleached, the dyes coloring the substrate are usually oxidatively decolorized using suitable oxidizing agents, such as hydrogen peroxide.

When dyeing hair—particularly when dyeing hair at home—the problem occurs that natural color nuances are completely covered, so that multi-tonal dyeing is difficult to achieve.

In order to give the hair a more natural appearance, it is known in the prior art to partially decolorize dyed hair by the targeted application of oxidizing agents. The hair sections ("strands") to which the oxidizing agents are applied are thus at least partially bleached, resulting in a multi-tonal hair color. In this case, the oxidizing agent is applied using a brush or a wand, the hair that is not to be treated optionally being protected by aluminum foil or a so-called "highlights cap" prior to the decolorizing.

Although this type of application solves the problem of dyeing hair in a manner that looks as natural as possible, it nevertheless only allows the application of "highlights". For "lowlights", that is to say darker sections, subsequent dyeing would have to take place. In the scenarios described above, therefore, a time-consuming second decolorizing and dyeing step would be necessary, which takes place after the first dyeing. Particularly in the case of home use, therefore, all of the hair would first have to be colored before the user can apply "highlights" or "lowlights". This is perceived by many consumers as time-consuming and also as frustrating, since the main color-changing step takes place at the start and is merely "corrected" in a second step.

It is therefore desirable to provide a method which enables multi-tonal dyeing in one dyeing step. The dyeing of the hair should be accompanied by the creation of "highlights" or "lowlights", so that a result is visible immediately after rinsing out the coloring agent.

BRIEF SUMMARY OF THE INVENTION

A method for oxidatively dyeing keratin fibers includes the following method steps in the specific order:
a) applying a cosmetic agent (M1) to the keratin fibers,
b) leaving the agent (M1) to act on the keratin fibers for a duration of from 30 seconds to 40 minutes,
c) applying a cosmetic agent (M2) to the keratin fibers to which the cosmetic agent (M1) was applied,
d) leaving the cosmetic agents (M1) and (M2) to act on the keratin fibers for a duration of from 1 to 70 minutes, and
e) rinsing out the cosmetic agents (M1) and (M2), characterized in that
    the cosmetic agent (M1) includes
        at least one oxidation dye precursor of the developer type (M1-1),
        at least one oxidation dye precursor of the coupler type (M1-2),
        at least one substantive dye (M1-3), and
        at least one thickening agent (M1-4), and
    the cosmetic agent (M2) includes
        at least one oxidation dye precursor (M2-1), and
        at least one oxidizing agent (M2-2).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that a partial pretreatment of fiber areas or strands leads to said area or strands being subsequently colored more or less intensely. Due to the pre-penetration or pretreatment of individual fiber areas or strands, the coloring agent applied directly thereafter dyes the hair in a multi-tonal manner, and a natural color result with "highlights" or "lowlights" is obtained immediately after the dyeing step.

According to the invention, the term "keratin fibers" is to be understood to mean fur, wool, feathers and human hair. In the context of the present invention, it is particularly preferred if the method according to the invention is used for dyeing human hair.

In addition, in the context of the present invention, the term "thickening agent" is to be understood to mean compounds which are able to bind liquids, in particular water, and to increase the viscosity of said liquids. In the context of the present invention, these also include gelling agents, which are able to thicken liquids so as to form compositions having a gel-like consistency or so as to form gels. According to the invention, gel-like cosmetic agents or gels are to be understood to mean dimensionally stable, easily deformable disperse systems consisting of at least two components, the gelling agent (usually a solid, colloidally dispersed substance comprising long or highly branched compounds) and a liquid (usually water) as the dispersing aid. The gelling agent forms a spatial network in the liquid, wherein the individual gel-forming compounds adhere to one another by primary and/or secondary valences at different spatial points.

According to the invention, method steps a) to e) are preferably carried out in the order specified above, with a time interval between the individual method steps of in each case from 0 to 60 minutes, preferably in each case from 0 to 40 minutes, in particular in each case from 0 to 30 minutes.

In the first method step (method step a)) of the method according to the invention, a cosmetic agent (M1) is applied to the fibers. Said cosmetic agent (M1), which hereinafter is also referred to as the pretreatment or pre-penetration agent, is left on the keratin fibers for a duration of from 30 seconds to 30 minutes (method step b) of the method according to the invention).

According to the invention, however, preference is given to shorter leave-in times of the pretreatment agent. Particularly preferred methods according to the invention are characterized in that the cosmetic agent (M1) in method step b) is left to act on the keratin fibers for a duration of from 30 seconds to 30 minutes, preferably from 30 seconds to 20 minutes, more preferably from 30 seconds to 18 minutes, in particular from 30 seconds to 15 minutes.

Pretreating keratin fibers with the cosmetic agent (M1) leads to the situation whereby, at these locations, ingredients of the pretreatment agent (M1) already adhere to the keratin fibers or have penetrated into the keratin fibers, so that the color result upon subsequent application of the cosmetic agent (M2) is enhanced or lightened at these locations. In this way, in one dyeing step, the hair is colored and at the same time a multi-tonal dyeing with lighter ("highlights") or darker ("lowlights") sections (strands) is produced.

It has been found that a pretreatment at slightly elevated temperatures can make the multi-tonal effects even more vibrant. Methods which are preferred according to the invention are characterized in that the cosmetic agent (M1) in method step b) is left to act at a temperature of from 20° C. to 120° C., in particular from 30° C. to 120° C. Temperatures of from 30° C. to 120° C., preferably from 40° C. to 120° C., can be achieved for example by using a hairdryer or a drying hood.

To achieve multi-tonal dyeing, the cosmetic agent (M1) should not be applied evenly to the keratin fibers. Preferably, the cosmetic agent (M1) will be applied only to individual regions, particularly preferably only to individual strands. Alternatively, the concentration of the cosmetic agent (M1) applied to individual strands can be varied. It is also possible to apply the cosmetic agent (M1) first of all evenly to all the keratin fibers and then to treat individual regions or strands with the cosmetic agent (M1) again. Treating individual regions/strands with the cosmetic agent (M1) multiple times is also possible according to the invention.

In this connection, it is particularly preferred if the cosmetic agent (M1) in method step a) is applied only to individual strands. According to the invention, the term "strands" will be understood to mean a section separated from the full head of keratin fibers, said strand consisting of at least 2, preferably at least 50, in particular at least 100 keratin fibers.

After the leave-in time of the pretreatment agent, the keratin fibers are not rinsed or towel-dried. Instead, in method step c) of the method according to the invention, a cosmetic agent (M2) is applied to the keratin fibers to which the cosmetic agent (M1) is still applied. In method step d) of the method according to the invention, the mixture of cosmetic agents (M1) and (M2) obtained by applying the cosmetic agent (M2) to the keratin fibers is left to act for a duration of from 1 to 70 minutes.

According to the invention, however, somewhat shorter leave-in times of the cosmetic agents (M1) and (M2) in method step d) are preferred. Particularly preferred methods according to the invention are characterized in that the cosmetic agents (M1) and (M2) in method step d) are left to act for a duration of from 1 to 60 minutes, preferably from 5 to 50 minutes, in particular from 10 to 45 minutes.

Since the cosmetic agent (M1) in method step b) of the method according to the invention has already been left on the keratin fibers for some time, said keratin fibers have a longer period of contact with the ingredients of the cosmetic agent (M1) than with those of the cosmetic agent (M2). If the cosmetic agent (M1) was applied only to individual strands or in individual regions, the ingredients of the cosmetic agent (M1) could have a more intense effect in these regions and thus could enhance or weaken the effect of the ingredients of the cosmetic agent (M2) in these regions, as a result of which a darker or lighter dyeing of these regions is achieved.

After rinsing out the cosmetic agents (M1) and (M2) in method step e) of the method according to the invention, a multi-tonal color result is obtained directly without having to carry out a further step.

The cosmetic agent (M1) or the pretreatment agent is an oxidative hair coloring agent which includes at least one oxidation dye precursor of the developer type (M1-1). According to the invention, the at least one oxidation dye precursor of the developer type (M1-1) is preferably selected from the group consisting of 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol and the physiologically acceptable salts thereof and mixtures thereof.

To obtain natural colorations, usually a plurality of oxidation dye precursors of the developer type must be used. Preferred cosmetic agents (M1) are therefore characterized in that the at least one oxidation dye precursor of the developer type (M1-1) is selected from at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis-(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazol-1-yl)propyl]amine; p-toluylenediamine/bis-(2-hydroxy-5-aminophenyl)methane; p-toluylenediamine/4-amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine N,N-bis-(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine N-(4-amino-3-methylphenyl)-N-[3-(1H-imidazol-1-yl)propyl]amine; 2-(2-hydroxyethyl)-p-phenylenediamine/bis-(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2- hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis-(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3-(1H-imidazol-1-yl)propyl]amine; bis-(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine and/or 4-amino-3-methylphenol/4,5-diamino-1-(2-hydroxyethyl)pyrazole and/or the physiologically acceptable salts thereof.

According to one particularly preferred embodiment of the first subject matter of the invention, the at least one oxidation dye precursor of the developer type (M1-1) is selected from the group consisting of p-toluylenediamine, 4-amino-3-methylphenol, 4,5-diamino-1-(2-hydroxyethyl)pyrazole, 2,4,5,6-tetraaminopyrimidine and/or the physiologically acceptable salts thereof and mixtures thereof. It has been found that the use of said specific oxidation dye precursors of the developer type (M1-1) in the pretreatment agents (M1) used in the context of the method according to the invention leads to particularly vibrant multi-tonal colorations which remain fast against washing, friction, sweat and UV.

Multi-tonal colorations of particularly pleasant appearance are obtained if the cosmetic agent (M1) includes the at least one oxidation dye precursor of the developer type (M1-1) in a total amount of from 0.002 to 6.0% by weight, preferably from 0.005 to 5.0% by weight, more preferably from 0.05 to 4.0% by weight, in particular from 0.01 to 3.5% by weight, based on the total weight of the cosmetic agent (M1). The aforementioned amounts of the developer component (M1-1) lead to multi-tonal colorations which have particularly intense and bright colors and a high resistance to environmental influences such as shampoos, UV light, sweat and friction.

The pretreatment agent (M1) includes as a further constituent at least one oxidation dye precursor of the coupler type (M1-2). In the context of oxidative dyeing, oxidation dye precursors of the coupler type do not on their own form any significant coloring, but rather require the presence of oxidation dye precursors of the developer type in order to achieve a sufficient coloring. In the context of the invention, oxidation dye precursors of the coupler type enable at least one substitution of a chemical radical of the coupler by the oxidized form of the developer component. This results in the formation of a covalent bond between the coupler component and the developer component.

In the context of the present invention, it is preferred if the at least one oxidation dye precursor of the coupler type (M1-2) is selected from the group consisting of m-aminophenol and derivatives thereof, o-aminophenol and derivatives thereof, m-diaminobenzene and derivatives thereof, o-diaminobenzene and derivatives thereof, di- and trihydroxybenzene derivatives, pyridine derivatives, naphthalene derivatives, morpholine derivatives, quinoxaline derivatives, pyrazole derivatives, indole derivatives, pyrimidine derivatives, methylenedioxybenzene derivatives and/or the physiologically acceptable salts thereof and mixtures thereof.

Preferred methods according to the invention are characterized in that the at least one oxidation dye precursor of the coupler type (M1-2) is selected from the group consisting of resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, 1-naphthol and/or the physiologically acceptable salts thereof and mixtures thereof. The aforementioned coupler components (M1-2), in combination with the at least one developer component (M1-1) in the pretreatment agent (M1), lead to particularly intense and stable multi-tonal color results.

According to the invention, the cosmetic agent (M1) preferably includes the at least one oxidation dye precursor of the coupler type (M1-2) in a total amount of from 0.002 to 4.0% by weight, preferably from 0.005 to 3.5% by weight, more preferably from 0.05 to 3.0% by weight, in particular from 0.01 to 2.0% by weight, based on the total weight of the cosmetic agent (M1). The aforementioned amounts of the coupler component (M1-2) in the pretreatment agents (M1) used in the context of the method according to the invention lead to particularly vibrant multi-tonal colorations which remain fast against washing, friction, sweat and UV.

In order to ensure a balanced and subtle shade formation, the pretreatment agents (M1) used in the context of the method according to the invention contain at least one substantive dye (M1-3). Substantive dyes are dyes which attach directly to the hair and require no oxidative process to develop the color. Substantive dyes are usually nitrophenylenediamines, nitroaminophenols, azo dyes, anthraquinones or indophenols.

According to one preferred embodiment of the first subject matter of the invention, the at least one substantive dye (M1-3) is selected from the group consisting of anionic substantive dyes, cationic substantive dyes, nonionic substantive dyes, and mixtures thereof.

In this connection, it may be provided according to the invention that the anionic substantive dye is selected from the group consisting of Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Tetrabromophenol Blue and/or the physiologically acceptable salts thereof.

In the context of this embodiment, it may also be provided that the cationic substantive dye is selected from the group consisting of Basic Blue 7, Basic Blue 26, Basic Violet 2 and Basic Violet 14, Basic Yellow 57, Basic Red 76, Basic Blue 99, Basic Brown 16 and Basic Brown 17 and HC Blue 16 and Basic Yellow 87, Basic Orange 31 and Basic Red 51 and/or the physiologically acceptable salts thereof.

In addition, it may also be provided in the context of this embodiment that the nonionic substantive dye is selected from the group consisting of HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4, 6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid, 2-amino-6-chloro-4-nitrophenol, 4-ethylamino-3-nitrobenzoic acid and 2-chloro-6-ethylamino-4-nitrophenol and/or the physiologically acceptable salts thereof, preferably 2-amino-6-chloro-4-nitrophenol and/or 4-amino-3-nitrophenol and/or the physiologically acceptable salts thereof.

In the context of the method according to the invention, pretreatment agents (M1) which are particularly preferably used contain at least one substantive dye (M1-3) which is selected from the group consisting of 2-amino-6-chloro-4-nitrophenol, HC Blue 12, HC Yellow 2, HC Violet 14D and/or the physiologically acceptable salts thereof and mixtures thereof. When using these specific substantive dyes, a particularly balanced and subtle shade formation is achieved during the method according to the invention or in the multi-tonal coloration.

According to the invention, the cosmetic agent (M1) preferably includes the at least one substantive dye (M1-3) in a total amount of from 0.00001 to 5.0% by weight, preferably from 0.00005 to 4.5% by weight, more preferably from 0.0001 to 4.0% by weight, yet more preferably from 0.0005 to 3.5% by weight, in particular from 0.001 to 3.0% by weight, based on the total weight of the cosmetic agent (M1). The aforementioned amounts of the substantive dyes lead to particularly balanced shades in the context of the multi-tonal coloration by the method according to the invention.

In order to set the desired viscosity, and to avoid any running of the cosmetic agent (M1) during application to the keratin fibers and during the leave-in time in method step b), the cosmetic agents (M1) contain at least one thickening agent.

According to one preferred embodiment of the first subject matter of the invention, the at least one thickening agent (M1-4) is selected from the group consisting of thickening polysaccharides, thickening synthetic polymers, thickening inorganic compounds and mixtures thereof.

In this connection, it may be provided according to the invention that the thickening polysaccharide is selected from the group consisting of xanthan, cellulose, cellulose derivatives, curdlan, algins, alginates, glucans, pullulans, amyloses, tragacanth, karaya gum, ghatti gum, agar, carrageenan, chitin, chitosan, gum arabic, gellan, guar gum, locust bean gum and mixtures thereof, preferably xanthan, celluloses, cellulose derivatives and mixtures thereof.

In the context of this embodiment, it may also be provided that the thickening synthetic polymer is selected from the group consisting of crosslinked homopolymers or copolymers of acrylic acid, methacrylic acid and salts and alkyl esters thereof, homopolymers or copolymers of acrylamides and/or methacrylamides, copolymers of acrylic acid and acrylamides and mixtures thereof, preferably crosslinked homopolymers or copolymers of acrylic acid, methacrylic acid and salts and alkyl esters thereof, crosslinked copolymers of ethoxylated alkyl esters of methacrylic acid and sulfonated acrylamides and salts thereof, and crosslinked copolymers of methacrylic acid, acrylamides and sulfonated acrylamides and salts thereof. Particular preference is given to the crosslinked copolymer known under the INCI name Ammonium Acryloyldimethyltaurate/Beheneth-25 Methacrylate Crosspolymer, which is commercially available for example under the trade name Aristoflex HMB from the company Clariant. In the context of this embodiment, particular preference is also given to the crosslinked copolymer having the INCI name Acrylates/C10-30 Alkyl Acrylate Crosspolymer, which is available under the trade name Carbopol from the company Lubrizol. In the context of this embodiment, preference is also given to the crosslinked copolymer known under the INCI name Polyacrylate Crosspolymer-11, which is commercially available under the trade name Aristoflex Velvet from the company Clariant.

In addition, it may also be provided in the context of this embodiment that the thickening anionic compound is selected from the group consisting of electrolytes, in particular sodium chloride and potassium chloride, phyllosilicates, magnesium aluminum silicates, optionally modified bentonites, in particular optionally modified smectites, and mixtures thereof.

In the context of the method according to the invention, cosmetic agents (M1) which are particularly preferably used contain at least one thickening agent (M1-4) selected from the group consisting of cellulose, cellulose derivatives, xanthan, crosslinked homopolymers or copolymers of acrylic acid, methacrylic acid and salts thereof, crosslinked copolymers of ethoxylated alkyl esters of methacrylic acid and sulfonated acrylamides and salts thereof, crosslinked copolymers of methacrylic acid, acrylamides and sulfonated acrylamides and salts thereof, and mixtures of said thickening agents. In order to be able to apply the pre-penetration agent (M1) in a clean and localized manner, a gel-like consistency of the agent has proven to be advantageous. The gel-like pretreatment agents (M1) on the one hand ensure that they can be easily and evenly distributed on the keratin fibers and do not lead to any bleeding or running during the leave-in time in method step b). In this way, it is possible for the pretreatment agent (M1) to be applied to and to act on narrow strands or regions, so that an excellent multi-tonal color result is achieved without any blurring of the strands caused by running of the pretreatment agent (M1).

In the context of the method according to the invention, it may also be particularly preferred if two different thickening agents (M1-4), selected from crosslinked homopolymers or copolymers of acrylic acid, methacrylic acid and salts thereof and xanthan, are used in the cosmetic agents (M1).

According to the invention, the cosmetic agent (M1) preferably includes the at least one thickening agent (M1-4) in a total amount of from 0.1 to 5.0% by weight, preferably from 0.3 to 4.5% by weight, more preferably from 0.5 to 4.0% by weight, yet more preferably from 0.7 to 3.5% by weight, in particular from 0.8 to 3.0% by weight, based on the total weight of the cosmetic agent (M1). The aforementioned amounts of thickening agents ensure a sufficient thickening so as to prevent any running of the pretreatment agent (M1) during the leave-in time in method step b) and any resulting blurring of the multi-tonal color result. Said amounts of thickening agent moreover ensure that the pretreatment agents (M1) can be easily and evenly distributed on the keratin fibers.

According to the invention, cosmetic agents (M1) which are preferably used have a dynamic viscosity of from 5000 to 90,000 mPa*s, preferably from 6000 to 80,000 mPa*s, more preferably from 8000 to 70,000 mPa*s, yet more preferably from 9000 to 60,000 mPa*s, in particular from 10,000 to 50,000 mPa*s, in each case measured using a Brookfield RDV II+, spindle no. 4, 4 rpm, 20° C.

In addition to the oxidation dye precursor(s) of the developer type and coupler type, the substantive dye(s) and the thickening agent(s), the cosmetic agent (M1) used in the method according to the invention may contain further ingredients.

According to the invention, the cosmetic agent (M1) preferably additionally includes at least one further compound, selected from the group consisting of (i) surfactants; (ii) glycols; (iii) alkalizing agents; and (iv) mixtures thereof.

In the context of the present invention, surfactants are amphiphilic (bifunctional) compounds which consist of at least one hydrophobic moiety and at least one hydrophilic moiety. A basic property of surfactants and emulsifiers is the oriented absorption at interfaces as well as the aggregation into micelles and the formation of lyotropic phases.

Surfactants which can be used in the context of the present invention are selected from the group consisting of nonionic surfactants, anionic surfactants, amphoteric surfactants, zwitterionic surfactants, cationic surfactants and mixtures thereof.

According to the invention, use is particularly preferably made in the method according to the invention of cosmetic agents (M1) which additionally contain at least one nonionic surfactant from the group consisting of (i) alkylene oxide addition products with alcohols having 8 to 30 carbon atoms or carboxylic acids having 8 to 30 carbon atoms, which in each case contain 2 to 30 mol of ethylene oxide per mole of alcohol or carboxylic acid; (ii) carboxylic acid esters of ethoxylated and/or propoxylated glycerol having 8 to 30 carbon atoms in the carboxylic acid chain and 1 to 30 mol of ethylene oxide and/or propylene oxide per mole of glycerol; and (iii) mixtures thereof.

Particularly preferred methods according to the invention are therefore characterized in that the cosmetic agents (M1) additionally contain at least one nonionic surfactant from the group consisting of carboxylic acid esters of ethoxylated and/or propoxylated glycerol having 8 to 30 carbon atoms in the carboxylic acid chain and 1 to 30 mol of ethylene oxide and/or propylene oxide per mole of glycerol in a total amount of from 0.1 to 10% by weight, preferably from 0.5 to 5% by weight, in particular from 0.8 to 3% by weight, based on the total weight of the cosmetic agent (M1).

Furthermore, the pretreatment agents (M1) may additionally contain at least one anionic surfactant. Preferred anionic surfactants are fatty acids, alkyl sulfates, alkyl ether sulfates and ether carboxylic acids having 10 to 20 C atoms in the alkyl group and up to 16 glycol ether groups in the molecule. The anionic surfactants are used in a total amount of from 0.1 to 45% by weight, more preferably from 1 to 30% by weight, in particular from 1 to 15% by weight, based on the total weight of the cosmetic agent (M1).

In addition, it is also possible that the pretreatment agents (M1) additionally contain at least one zwitterionic and/or amphoteric surfactant. Preferred zwitterionic surfactants are betaines, N-alkyl-N,N-dimethyl ammonium glycinates, N-acylaminopropyl-N,N-dimethyl ammonium glycinates, and 2-alkyl-3-carboxymethyl-3-hydroxyethylimidazolines. A particularly preferred zwitterionic surfactant is known under the INCI name Cocamidopropyl Betaine.

Preferred amphoteric surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids. Particularly preferred amphoteric surfactants are N-cocoalkylaminopropionate, cocoacylaminoethylaminopropionate and C12-C18 acyl sarcosine. The zwitterionic and/or amphoteric surfactants are used in a total amount of from 0.1 to 45% by weight, preferably from 1 to 30% by weight, in particular from 1 to 15% by weight, based on the total weight of the cosmetic agent (M1).

The pretreatment agents (M1) may additionally contain at least one compound from the glycol group. According to the invention, the term "glycols" will be understood to mean compounds which have 2 hydroxyl groups.

Glycols which are suitable according to the invention are selected from the group consisting of ethylene glycol, propylene glycol (1,2-propanediol), ethylene glycol monomethyl ether, trimethylene glycol, triethylene glycol, polyethylene glycol, neopentyl glycol and mixtures thereof.

Particularly preferred methods according to the invention are characterized in that the cosmetic agents (M1) additionally contain at least one glycol from the group consisting of ethylene glycol, propylene glycol (1,2-propanediol), polyethylene glycol, and mixtures thereof, in a total amount of from 0.1 to 10% by weight, preferably from 0.5 to 5% by weight, in particular from 0.8 to 3% by weight, based on the total weight of the cosmetic agent (M1).

The pretreatment agents (M1) used in the context of the method according to the invention may also contain at least one alkalizing agent.

Organic alkalizing agents which can be used according to the invention are preferably selected from alkanolamines of primary, secondary or tertiary amines with a C2-C6 alkyl main body, which carries at least one hydroxyl group. Alkanolamines which are very particularly preferred according to the invention are selected from the group consisting of 2-aminoethan-1-ol (monoethanolamine), 2-amino-2-methylpropan-1-ol and 2-amino-2-methylpropane-1,3-diol, and mixtures thereof. One particularly preferred alkanolamine is monoethanolamine. Suitable basic amino acids are lysine, arginine and ornithine. Inorganic alkalizing agents according to the invention are preferably selected from the group consisting of sodium hydroxide, potassium hydroxide, calcium hydroxide, barium hydroxide, sodium phosphate, potassium phosphate, sodium silicate, potassium silicate, sodium carbonate and potassium carbonate.

Methods which are particularly preferred according to the invention are characterized in that the cosmetic agent (M1) includes one or more alkalizing agents from the group consisting of sodium hydroxide, potassium hydroxide, ammonia, monoethanolamine and 2-amino-2-methylpropanol in a total amount of from 0.05 to 8.0% by weight, preferably from 0.1 to 6.0% by weight, in particular from 0.5 to 5.0% by weight, based on the total weight of the cosmetic agent (M1).

The pretreatment agents (M1) used in the context of the method according to the invention usually have a basic pH, in particular between pH 7.0 and pH 14. These pH values are necessary so as to ensure that the outer cuticle (cuticula) opens up and enables a penetration of the oxidation dye precursors into the hair.

Methods which are preferred according to the invention are therefore characterized in that the cosmetic agent (M1) has a pH of from pH 7.0 to pH 14.0, preferably from pH 8.8 to pH 11.0, more preferably from pH 9.0 to pH 10.8, in particular from pH 9.2 to pH 10.5. The setting of said pH values may preferably take place using the aforementioned alkalizing agents.

In order to enable the natural and multi-tonal color result to emerge in a particularly apparent and surprising manner at the end of the method according to the invention, the pretreatment agent (M1) on its own is preferably not able to be used as a separate bleaching, lightening or coloring agent. To this end, it is particularly advantageous if the cosmetic agents (M1) are free of oxidizing agents, in particular are free of hydrogen peroxide and/or persulfates.

In the context of the present invention, the expression "free of" means that no intentionally added oxidizing agents are contained in the cosmetic agents (M1). Nevertheless, traces of said oxidizing agents may be incorporated in the cosmetic agents (M1) as contamination or as an accompanying substance via other raw materials. More specifically, therefore, "free of" means that the cosmetic agents (M1) contain less than 1% by weight, preferably less than 0.5% by weight, more preferably less than 0.25% by weight, yet more preferably less than 0.1% by weight, in particular less than 0.01% by weight oxidizing agents, based on the total weight of the cosmetic agent (M1).

Methods which are preferred according to the invention are therefore characterized in that the cosmetic agent (M1) used in method step a) includes less than 1% by weight, preferably less than 0.5% by weight, more preferably less than 0.25% by weight, yet more preferably less than 0.1% by weight, in particular less than 0.01% by weight peroxo compounds, based on the total weight of the cosmetic agent (M1). In the context of the present invention, peroxo compounds will be understood to mean compounds which contain at least one peroxide anion $O_2^{2-}$ and/or at least one peroxy group O O.

Methods which are particularly preferred according to the invention are characterized in that the cosmetic agent (M1) used in method step a) includes less than 1% by weight, preferably less than 0.5% by weight, more preferably less than 0.25% by weight, yet more preferably less than 0.1% by weight, in particular less than 0.01% by weight hydrogen peroxide, based on the total weight of the cosmetic agent (M1).

In method step c) of the method according to the invention, a cosmetic agent (M2) is applied to the keratin fibers to which the agent (M1) is still applied. Said cosmetic agent (M2), which hereinafter will also be referred to as the coloring agent, includes at least one oxidation dye precursor (M2-1) and at least one oxidizing agent (M2-2).

Preferred cosmetic agents (M2) contain at least one oxidation dye precursor of the developer and/or coupler type. According to the invention, preference is given to such methods according to the invention in which the cosmetic agent (M2) includes one or more oxidation dye precursors of the developer type as the oxidation dye precursor (M2-1).

Suitable and preferred oxidation dye precursors of the developer type have already been described in detail in connection with the pretreatment agent (M1). The same compounds can also be used in the coloring agents (M2). However, it has been found that the use of specific oxidation dye precursors of the developer type in specific amounts in the coloring agents (M2) is highly suitable for producing particularly vibrant multi-tonal colorations which remain fast against washing, friction, sweat and UV.

Particularly preferred methods according to the invention are characterized in that the cosmetic agent (M2) includes as the oxidation dye precursor of the developer type one or more compounds from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine and/or the physiologically acceptable salts thereof in a total amount of from 0.1 to 3.5% by weight, preferably from 0.3 to 2.8% by weight, more preferably from 0.4 to 2.1% by weight, in particular from 0.5 to 1.6% by weight, based on the total weight of the cosmetic agent (M2).

Other particularly preferred methods according to the invention are characterized in that the cosmetic agent (M2) includes as the oxidation dye precursor of the developer type one or more compounds from the group consisting of bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol and/or the physiologically acceptable salts thereof in a total amount of from 0.0005 to 3.5% by weight, preferably from 0.001 to 2.75% by weight, more preferably from 0.0025 to 2.5% by weight, in particular from 0.005 to 2.0% by weight, based on the total weight of the cosmetic agent (M2).

Other particularly preferred methods according to the invention are characterized in that the cosmetic agent (M2) includes as the oxidation dye precursor of the developer type one or more compounds from the group consisting of 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and/or the physiologically acceptable salts thereof in a total amount of from 0.1 to 3.5% by weight, preferably from 0.3 to 2.8% by weight, more preferably from 0.4 to 2.1% by weight, in particular from 0.5 to 1.6% by weight, based on the total weight of the cosmetic agent (M2).

Other particularly preferred methods according to the invention are characterized in that the cosmetic agent (M2) includes as oxidation dye precursors of the developer type at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis-(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazol-1-yl)propyl]amine; p-toluylenediamine/bis-(2-hydroxy-5-aminophenyl)methane; p-toluylenediamine/4-amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis-(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methylphenyl)-N-[3-(1H-imidazol-1-yl)propyl]amine; 2-(2-hydroxyethyl)-p-phenylenediamine/bis-(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis-(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3-(1H-imidazol-1-yl)propyl]amine; 2-methoxymethyl-p-phenylenediamine/bis-(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine and/or 4-amino-3-methylphenol/4,5-diamino-1-(2-hydroxyethyl)pyrazole and/or the physiologically acceptable salts thereof.

According to the invention, the cosmetic agent (M2) preferably also includes one or more oxidation dye precursors of the coupler type.

Coupler components which are preferably used according to the invention are selected from one of the following classes: m-aminophenol, o-aminophenol, m-diaminobenzene, o-diaminobenzene and/or derivatives thereof; naphthalene having at least one hydroxyl group; di- or trihydroxybenzene; pyridine derivatives; pyrimidine derivatives; certain indole derivatives and indoline derivatives; pyrazolone derivatives (for example 1-phenyl-3-methylpyrazol-5-one); morpholine derivatives (for example 6-hydroxybenzomorpholine or 6-aminobenzomorpholine); quinoxaline derivatives (for example 6-methyl-1,2,3,4-tetrahydroquinoxaline), and mixtures of two or more compounds from one or more of said classes.

Preferred m-aminophenol coupler components are selected from at least one compound from the group consisting of 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and the physiologically acceptable salts thereof. Preferred m-diaminobenzene coupler components are selected from at least one compound from the group consisting of m-phenylenediamine, 2-(2,4-diaminophenoxy)ethanol, 1,3-bis-(2,4-diaminophenoxy)propane, 1-methoxy-2-amino-4-(2'-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and the physiologically acceptable salts thereof. Preferred o-diaminobenzene coupler components are selected from at least one compound from the group consisting of 3,4-diaminobenzoic acid and 2,3-diamino-1-methylbenzene and the physiologically acceptable salts thereof. Preferred naphthalene derivatives having at least one hydroxyl group are selected from at least one compound from the group consisting of 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene. Preferred di- or trihydroxybenzenes and derivatives thereof are selected from at least one compound from the group consisting of resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene. Preferred pyridine derivatives are selected from at least one compound from the group consisting of 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2, 3-diamino-6-methoxypyridine, 3,5-diamino-2,6-dimethoxypyridine, 3, 4-diaminopyridine, 2-(2-methoxyethyl)amino-3-amino-6-methoxypyridine, 2-(4'-methoxyphenyl)amino-3-aminopyridine and the physiologically acceptable salts thereof. Preferred pyrimidine derivatives are selected from at least one compound from the group consisting of 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically acceptable salts thereof. Preferred indole derivatives are selected from at least one compound from the group consisting of 4-hydroxyindole, 6-hydroxyindole and 7-hydroxyindole and the physiologically acceptable salts thereof. Preferred indoline derivatives are selected from at least one compound from the group consisting of 4-hydroxyindoline, 6-hydroxyindoline and 7-hydroxyindoline and the physiologically acceptable salts thereof.

Coupler components which are particularly preferably used according to the invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2, 7-dihydroxynaphthalene, 1, 7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or the physiologically acceptable salts thereof. Very particular preference is given to resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine and 1-naphthol as well as the physiologically acceptable salts thereof.

The coupler components are contained in the cosmetic agent (M2) preferably in a total amount of from 0.0001 to 2.0% by weight, in particular from 0.001 to 1.25% by weight, based on the total weight of the cosmetic agent (M2).

The use of specific oxidation dye precursors of the coupler type in specific amounts in the coloring agents (M2) results in multi-tonal colorations which have particularly vibrant colors that remain fast against washing, friction, sweat and UV.

Methods which are preferred according to the invention are therefore characterized in that the cosmetic agent (M2) includes as the oxidation dye precursor of the coupler type one or more compounds from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol and/or the physiologically acceptable salts thereof in a total amount of from 0.001 to 2.5% by weight, preferably from 0.0025 to 2.0% by weight, more preferably from 0.0025 to 1.5% by weight, in particular from 0.005 to 1.25% by weight, based on the total weight of the cosmetic agent (M2).

Other methods which are preferred according to the invention are characterized in that the cosmetic agent (M2) includes as the oxidation dye precursor of the coupler type one or more compounds from the group consisting of 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene and/or the physiologically acceptable salts thereof in a total amount of from 0.001 to 2.5% by weight, preferably from 0.0025 to 2.0% by weight, more preferably from 0.0025 to 1.5% by weight, in particular from 0.005 to 1.25% by weight, based on the total weight of the cosmetic agent (M2).

Other methods which are preferred according to the invention are characterized in that the cosmetic agent (M2) includes as the oxidation dye precursor of the coupler type one or more compounds from the group consisting of resorcinol, 2-methylresorcinol and/or 4-chlororesorcinol in a total amount of from 0.001 to 2.5% by weight, preferably from 0.0025 to 2.0% by weight, more preferably from 0.0025 to 1.5% by weight, in particular from 0.005 to 1.25% by weight, based on the total weight of the cosmetic agent (M2).

Other methods which are preferred according to the invention are characterized in that the cosmetic agent (M2) includes as the oxidation dye precursor of the coupler type one or more compounds from the group consisting of 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one and/or the physiologically acceptable salts thereof in a total amount of from 0.001 to 2.5% by weight, preferably from 0.0025 to 2.0% by weight, more preferably from 0.0025 to 1.5% by weight, in particular from 0.005 to 1.25% by weight, based on the total weight of the cosmetic agent (M2).

Other methods which are preferred according to the invention are characterized in that the cosmetic agent (M2) includes as the oxidation dye precursor of the coupler type at least one of the following combinations: resorcinol/3-aminophenol; 2-methylresorcinol/3-aminophenol; 4-chlororesorcinol/3-aminophenol; resorcinol/5-amino-2-methylphenol; 2-methylresorcinol/5-amino-2-methylphenol; 4-chlororesorcinol/5-amino-2-methylphenol; resorcinol/2-hydroxy-4-aminophenoxyethanol; 2-methylresorcinol/2-hydroxy-4-aminophenoxyethanol; 4-chlororesorcinol/2-hydroxy-4-aminophenoxyethanol; resorcinol/2-amino-3-hydroxypyridine; 2-methylresorcinol/2-amino-3-hydroxypyridine; 4-chlororesorcinol/2-amino-3-hydroxypyridine; resorcinol/3-amino-2-methylamino-6-methoxypyridine; 2-methylresorcinol/3-amino-2-methylamino-6-methoxypyridine; 4-chlororesorcinol/3-amino-2-methylamino-6-methoxypyridine; resorcinol/2,6-dihydroxy-3,4-dimethylpyridine; 2-methylresorcinol/2,6-dihydroxy-3,4-dimethylpyridine and/or 4-chlororesorcinol/2,6-dihydroxy-3,4-dimethylpyridine and/or the physiologically acceptable salts thereof.

Preferably, the pretreatment agent (M1) includes the oxidation dye precursors of the developer type (M1-1) in a higher total substance amount than the cosmetic agent (M2) includes the oxidation dye precursors (M2-1). This leads to particularly intense and vibrant multi-tonal colorations, which moreover have a high resistance to environmental influences, such as for example shampoos, sweat, UV light or friction.

According to one particularly preferred embodiment of the present invention, the ratio of the total substance amount of all oxidation dye precursors of the developer type (M1-1) in the cosmetic agent (M1) to the total substance amount of all oxidation dye precursors (M2-1) in the cosmetic agent (M2) has a value (M1-1)/(M2-1) of from 1:5 to 1:2, preferably from 1:1 to 2:1, more preferably from 80:1 to 120:1, yet more preferably from 180:1 to 250:1, in particular from 400:1 to 600:1.

A variation of the shades of the multi-tonal coloration is possible by suitably selecting the oxidation dye precursors used in the cosmetic agents (M1) and (M2). For a very natural-looking multi-tonal coloration with soft transitions, preference is given to methods according to the invention in which the cosmetic agents (M1) and (M2) contain identical oxidation dye precursors of the developer type and of the coupler type.

If greater contrasts are desired, which are expressed in a more luminous multi-tonal appearance of the coloration, methods according to the invention in which the cosmetic agents (M1) and (M2) contain different oxidation dye precursors of the developer type have proven to be effective.

In the context of the method according to the invention, it may be provided that the cosmetic agents (M1) and (M2) contain identical ingredients. Preferably, however, the cosmetic agents (M1) and (M2) differ from one another in at least one ingredient.

The coloring agent (M2) may additionally contain substantive dyes in order to ensure a balanced shading of the multi-tonal colorations. According to one preferred embodiment of the subject matter of the invention, the cosmetic agent (M2) additionally includes at least one substantive dye from the group consisting of anionic substantive dyes, cationic substantive dyes, nonionic substantive dyes, and mixtures thereof.

Suitable and preferred substantive dyes have already been described in detail in connection with the cosmetic agent (M1). The same compounds can also be used in the coloring agents (M2). However, it has been found that the use of specific substantive dyes in specific amounts in the coloring agents (M2) is particularly suitable, since in this case a particularly balanced shading of the multi-tonal colorations can be ensured.

In the context of one embodiment of the method according to the invention, therefore, cosmetic agents (M2) which are particularly preferably used additionally contain at least one substantive dye which is selected from the group consisting of 2-amino-6-chloro-4-nitrophenol, HC Blue 12, HC Yellow 2, HC Violet 14D and/or the physiologically acceptable salts thereof and mixtures thereof.

In the context of this embodiment, methods according to the invention are characterized in that the cosmetic agent (M2) includes the at least one substantive dye in a total amount of from 0.00005 to 2.0% by weight, preferably from 0.00001 to 1.75% by weight, in particular from 0.0005 to 1.5% by weight, based on the total weight of the cosmetic agent (M2).

The coloring agents (M2) may also contain additional active substances, auxiliaries and additives in order to improve the coloring performance and to adjust other desired properties of the cosmetic agents (M2).

According to the invention, the cosmetic agent (M2) therefore preferably additionally includes at least one further compound selected from the group consisting of (i) thickening agents; (ii) linear or branched, saturated or unsaturated alcohols having 8 to 20 carbon atoms; (iii) surfactants; (iv) alkalizing agents; and (v) mixtures thereof.

It has proven to be advantageous if the cosmetic agents (M2) also contain at least one thickening agent. In principle, there are no restrictions with regard to said thickening agents. Suitable thickening agents are the compounds mentioned in connection with the pretreatment agent (M1), which can likewise be used to thicken the coloring agents (M2). In addition, use may also be made of the organic and inorganic thickening agents listed below.

Suitable thickening agents are anionic, synthetic polymers; cationic, synthetic polymers and nonionic, synthetic polymers, such as polyvinyl alcohol or polyvinylpyrrolidone.

The cosmetic agents (M2) used in the method according to the invention may also contain as thickening agents zwitterionic polymers which are selected from the group consisting of
- copolymers of dimethyl diallyl ammonium salts and acrylic acid, for example Polyquaternium-22,
- copolymers of dimethyl diallyl ammonium salts and methacrylic acid,
- copolymers of N,N,N-trimethyl-3-[(2-methyl-1-oxo-2-propen-1-yl)amino]-1-propanaminium salts and acrylic acid,
- copolymers of N,N,N-trimethyl-3-[(2-methyl-1-oxo-2-propen-1-yl)amino]-1-propanaminium salts and methacrylic acid,
- copolymers of N,N,N-trimethyl-2-[(2-methyl-1-oxo-2-propen-1-yl)amino]-1-ethanaminium salts and acrylic acid,
- copolymers of N,N,N-trimethyl-2-[(2-methyl-1-oxo-2-propen-1-yl)amino]-1-ethanaminium salts and methacrylic acid,
- copolymers of N,N,N-trimethyl-3-[(2-methyl-1-oxo-2-propen-1-yl)amino]-1-propanaminium salts, acrylic acid and acrylamide, for example Polyquaternium-53,
- copolymers of N,N,N-trimethyl-3-[(2-methyl-1-oxo-2-propen-1-yl)amino]-1-propanaminium salts, methacrylic acid and acrylamide,
- copolymers of 1-ethenyl-3-methyl-1H-imidazolium salts, 1-ethenyl-1H-imidazole, 1-ethenyl-2-pyrrolidinone and methacrylic acid, for example Polyquaternium-86,
- copolymers of 1-ethenyl-3-methyl-1H-imidazolium salts, 1-ethenyl-1H-imidazole, 1-ethenyl-2-pyrrolidinone and acrylic acid.

Mixtures of the aforementioned zwitterionic polymers can also be used to thicken the cosmetic agents (M2).

The coloring agents (M2) used according to the invention in method step c) may contain linear or branched, saturated or unsaturated alcohols having 8 to 20 carbon atoms. It has been found that the additional presence of these higher-chain alcohols can further improve the multi-tonal color result of the method according to the invention. Therefore, it is preferred if the cosmetic agents (M2) used in the method according to the invention additionally contain one or more alcohols from the group consisting of arachyl alcohol (eisocan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol).

Particularly suitable cosmetic agents (M2) contain one or more higher-chain alcohols of the aforementioned group in a total amount of from 1.0 to 10.0% by weight, preferably from 1.4 to 8.5% by weight, more preferably from 1.8 to 8.0% by weight, in particular from 2.0 to 7.0% by weight, based on the total weight of the cosmetic agent (M2).

Preferably, the coloring agents (M2) are provided as a liquid preparation and these agents therefore additionally contain an added surface-active substance, such surface-active substances being called surfactants or emulsifiers depending on the field of use. They are preferably selected from anionic, cationic, zwitterionic, amphoteric and nonionic surfactants and emulsifiers.

In the context of this embodiment, it may be provided that the anionic surfactant is selected from the group consisting of alkyl sulfates and alkyl polyglycol ether sulfates of formula R2-O(CH2-CH2O)X—OSO3H, in which R2 is a linear alkyl group having 8 to 30 carbon atoms and x=0 or 1 to 12, salts of linear and branched carboxylic acids having 8 to 30 carbon atoms, ethercarboxylic acids of formula R3-O—(CH2-CH2O)x-CH2-COOH, in which R3 is a linear alkyl group having 8 to 30 C atoms and x=0 or 1 to 16, and mixtures thereof. The anionic surfactants are preferably used in a total amount of from 0.1 to 45% by weight, preferably from 1 to 30% by weight, in particular from 1 to 15% by weight, based on the total amount of the cosmetic agent (M2).

In this connection, it may also be provided according to the invention that the nonionic surfactant is selected from the group consisting of ethoxylated alcohols and carboxylic acids having 8 to 13 carbon atoms and 2 to 30 ethylene oxide units, addition products of 5 to 60 mol ethylene oxide with castor oil and hydrogenated castor oil, alkyl polyglucosides of formula R10-[G]p, in which R1 is an alkyl and/or alkenyl radical having 4 to 22 carbon atoms, G is a sugar radical having 5 or 6 carbon atoms and p represents numbers from 1 to 10, monoethanolamides of carboxylic acids having 8 to 30 carbon atoms, and mixtures thereof.

In addition, it may also be provided in the context of this embodiment that the amphoteric surfactant is selected from the group consisting of amphoacetates with carboxylic acid radicals having 8 to 30 carbon atoms, N-alkyl glycines, N-alkylpropionic acids, N-alkylamidobutyric acids, N-alkyliminodipropionic acids, N-hydroxyethyl-N-alkylamidopropyl glycines, N-alkyl taurines, N-alkyl sarcosines, 2-alkylaminopropionic acids, alkylaminoacetic acids, and mixtures thereof.

In the context of this embodiment, it may also be provided that the zwitterionic surfactant is selected from the group consisting of betaines, N-alkyl-N,N-dimethyl ammonium glycinates, N-acyl-amidopropyl-N,N-dimethyl ammonium glycinates, 2-alkyl-3-carboxymethyl-3-hydroxyethylimidazolines, and mixtures thereof.

The nonionic and/or zwitterionic and/or amphoteric surfactants are preferably used in a total amount of from 0.1 to 45% by weight, preferably from 1 to 30% by weight, in particular from 1 to 15% by weight, based on the total amount of the cosmetic agent (M2).

The cosmetic agent (M2) may also contain at least one alkalizing agent. Suitable alkalizing agents and the total amounts thereof that can be used have already been mentioned in connection with the pretreatment agent (M1). The setting of a basic pH using the at least one alkalizing agent is necessary so as to ensure that the outer cuticle (cuticula) opens up and enables a penetration of the oxidation dye precursors into the hair.

Methods which are preferred according to the invention are therefore characterized in that the cosmetic agent (M2) has a pH of from pH 7.0 to pH 14.0, preferably from pH 8.8 to pH 11.0, more preferably from pH 9.0 to pH 10.8, in particular from pH 9.2 to pH 10.5.

In order to achieve a vibrant multi-tonal coloration, it is advantageous if the sequential application of the cosmetic agents (M1) and (M2) does not lead to considerable pH fluctuations since this may lead to insufficient penetration of the keratin fibers and thus also to an impaired color result. Preference is therefore given to methods according to the invention in which the cosmetic agent (M1) and the cosmetic agent (M2) have identical pH values.

The oxidation dye precursors (developers and couplers) themselves are not colored. The formation of the actual dyes takes place only in the course of application as a result of the oxidation dye precursors coming into contact with an oxidizing agent (preferably hydrogen peroxide). In a chemical reaction, the developers used as oxidation dye precursors (such as for example p-phenylenediamine derivatives or p-aminophenol derivatives) are first transformed oxidatively by hydrogen peroxide into a reactive intermediate stage, also known as quinoneimine or quinonediimine, which then reacts with the couplers in an oxidative coupling reaction to form the respective dye.

The cosmetic agents (M2) therefore additionally contain one or more oxidizing agents (M2 2). Suitable oxidizing agents are persulfates, peroxodisulfates, chlorites, hypochlorites and in particular hydrogen peroxide and/or one of the solid addition products thereof with organic or inorganic compounds.

Methods which are preferred according to the invention are therefore characterized in that the cosmetic agent (M2) includes at least one oxidizing agent (M2-2) from the group consisting of persulfates, peroxodisulfates, chlorites, hypochlorites, hydrogen peroxide and the solid addition products thereof with urea, melamine, polyvinylpyrrolidone and sodium borate, preferably hydrogen peroxide, in a total amount of from 0.5 to 10% by weight, preferably from 1.0 to 10% by weight, in particular from 1.5 to 10% by weight, based on the total weight of the cosmetic agent (M2). If hydrogen peroxide and the solid addition products thereof are used as the oxidizing agent, the aforementioned total amount is calculated on 100% strength H2O2.

In a further preferred embodiment, the cosmetic agent (M2) is an agent for coloring and optionally at the same time lightening keratin fibers, which includes hydrogen peroxide in a total amount of from 0.5 to 15% by weight, preferably from 1.0 to 12.5% by weight, more preferably from 1.5 to 10% by weight, in particular from 2.0 to 6.5% by weight, based on the total weight of the cosmetic agent (M2). The aforementioned total amount of hydrogen peroxide is based here on 100% strength H2O2.

In order to achieve an enhanced lightening and bleaching effect, the cosmetic agent (M2) may also contain at least one peroxo salt. Suitable peroxo salts are inorganic peroxo compounds, preferably selected from the group consisting of ammonium peroxodisulfate, alkali metal peroxodisulfates, ammonium peroxomonosulfate, alkali metal peroxomonosulfates, alkali metal peroxodiphosphates, alkaline earth metal peroxides, and mixtures thereof. Particular preference is given to peroxodisulfates, in particular ammonium peroxodisulfate, potassium peroxodisulfate and sodium peroxodisulfate.

The aforementioned peroxo salts are contained in a total amount of from 0.5 to 20% by weight, preferably from 1 to 12.5% by weight, more preferably from 2.5 to 10% by weight, in particular from 3 to 6% by weight, based on the total weight of the cosmetic agent (M2).

In order to prevent a premature, undesired reaction of the oxidation dye precursors by the oxidizing agent, the oxidation dye precursors and the oxidizing agents are advantageously packaged separately from one another and are only brought into contact just prior to application. Usually, therefore, oxidative coloring agents are sold in the form of a two-component "kit" (multicomponent packaging unit), wherein the first component includes the oxidation dye precursors and optionally substantive dyes as well as an alkalizing agent (for example ammonia) and the second component includes the oxidizing agent.

In a further embodiment of the present invention, preference is therefore given to cosmetic agents (M2) which are characterized in that they are prepared immediately prior to application by mixing at least two preparations, wherein the at least two preparations are provided in at least two separately packaged containers, and wherein one container includes a coloring agent (M2a) that includes at least one oxidation dye precursor in a cosmetic carrier, and a further container includes an oxidizing agent preparation (M2b) that includes at least one oxidizing agent.

The coloring agent (M2a) in this case preferably includes the oxidation dye precursors of the developer type and/or coupler type mentioned above in connection with the cosmetic agent (M2), optionally at least one substantive dye and optionally at least one active substance, auxiliary or additive mentioned above in connection with the cosmetic agent (M2). The oxidizing agent preparation (M2b) preferably includes an oxidizing agent in the form of hydrogen peroxide and/or one of the solid addition products thereof with organic or inorganic compounds, such as urea, melamine and sodium borate.

Such oxidizing agent preparations (M2b) are preferably aqueous, flowable oxidizing agent preparations. Preferred preparations (M2b) are characterized in that the flowable oxidizing agent preparation (M2b) includes from 40 to 90% by weight, preferably from 50 to 90% by weight, more preferably from 55 to 89% by weight, yet more preferably from 60 to 87% by weight, in particular from 65 to 85% by weight water, based on the total weight of the oxidizing agent preparation (M2b).

Preferably, the total amount of oxidizing agent, in particular hydrogen peroxide, in the oxidizing agent preparation (M2b) is from 0.5 to 12% by weight, preferably from 1.0 to 10% by weight, in particular from 1.5 to 6.0% by weight, based on the total weight of the oxidizing agent preparation (M2b). If hydrogen peroxide and the solid addition products thereof are used as the oxidizing agent, the aforementioned total amount is calculated on 100% strength H2O2.

According to the invention, the oxidizing agent preparation (M2b) can also be applied to the hair together with a catalyst, which activates the oxidation of the dye precursors. Such catalysts are for example specific enzymes, iodides, quinones or metal ions.

It has proven to be advantageous if the oxidizing agent preparations (M2b) additionally contain at least one stabilizer or complexing agent for stabilizing the oxidizing agent, in particular the hydrogen peroxide. Particularly preferred stabilizers are in particular EDTA and EDDS as well as phosphonates, in particular 1-hydroxyethane 1,1-diphosphonate (HEDP) and/or ethylenediamine tetramethylenephosphonate (EDTMP) and/or diethylenetriamine pentamethylenephosphonate (DTPMP) or the sodium salts thereof.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for oxidatively dyeing keratin fibers, wherein the method comprises the following method steps in the specified order:
   a) applying a cosmetic agent (M1) to the keratin fibers,
   b) leaving the agent (M1) to act on the keratin fibers for a duration of from 30 seconds to 40 minutes,
   c) applying a cosmetic agent (M2) to the keratin fibers to which the cosmetic agent (M1) was applied,
   d) leaving the cosmetic agents (M1) and (M2) to act on the keratin fibers for a duration of from 1 to 70 minutes, and
   e) rinsing out the cosmetic agents (M1) and (M2),
   wherein
      the cosmetic agent (M1) includes
         at least one oxidation dye precursor of the developer type (M1-1),
         at least one oxidation dye precursor of the coupler type (M1-2),
         at least one substantive dye (M1-3), and
         at least one thickening agent (M1-4), and
      the cosmetic agent (M2) includes
         at least one oxidation dye precursor (M2-1), and
         at least one oxidizing agent (M2-2).

2. The method according to claim 1, wherein cosmetic agent (M1) in method step b) is left to act on the keratin fibers for a duration of from 30 seconds to 30 minutes.

3. The method according to claim 1, wherein cosmetic agent (M1) in method step a) is applied only to individual strands.

4. The method according to claim 1, wherein cosmetic agents (M1) and (M2) in method step d) are left to act for a duration of from 1 to 60 minutes.

5. The method according to claim 1, wherein cosmetic agent (M1) includes the at least one oxidation dye precursor of the developer type (M1-1) in a total amount of from 0.002 to 6.0% by weight based on the total weight of the cosmetic agent (M1).

6. The method according to claim 1, wherein cosmetic agent (M1) includes the at least one oxidation dye precursor of the coupler type (M1-2) in a total amount of from 0.002 to 4.0% by weight based on the total weight of the cosmetic agent (M1).

7. The method according to claim 1, wherein cosmetic agent (M1) includes the at least one substantive dye (M1-3) in a total amount of from 0.00001 to 5.0% by weight based on the total weight of the cosmetic agent (M1).

8. The method according to claim 1, wherein the at least one thickening agent (M1-4) is selected from the group consisting of cellulose, cellulose derivatives, xanthan, crosslinked homopolymers or copolymers of acrylic acid, methacrylic acid and salts thereof, crosslinked copolymers of ethoxylated alkyl esters of methacrylic acid and sulfonated acrylamides and salts thereof, crosslinked copolymers of methacrylic acid, acrylamides and sulfonated acrylamides and salts thereof, and mixtures of said thickening agents.

9. The method according to claim 1, wherein the cosmetic agent (M1) includes the at least one thickening agent (M1-4) in a total amount of from 0.1 to 5.0% by weight, based on the total weight of the cosmetic agent (M1).

10. The method according to claim 1, wherein the cosmetic agent (M1) has a dynamic viscosity of from 5000 to 90,000 mPa*s measured using a Brookfield RDV II+, spindle no. 4, 4 rpm, 20° C.

11. The method according to claim 1, wherein cosmetic agent (M1) has a pH of from 7.0 to 14.0.

12. The method according to claim 1, wherein cosmetic agent (M2) includes as oxidation dye precursor (M2-1) at least one oxidation dye precursor of the developer and/or coupler type.

13. The method according to claim 1, wherein a ratio of the substance amount of all oxidation dye precursors of the developer type (M1-1) in the cosmetic agent (M1) to the total amount of all oxidation dye precursors (M2-1) in the cosmetic agent (M2) has a value (M1 1):(M2 1) of from 1:5 to 1:2.

14. The method according to claim 1, wherein a ratio of the substance amount of all oxidation dye precursors of the developer type (M1-1) in the cosmetic agent (M1) to the total amount of all oxidation dye precursors (M2-1) in the cosmetic agent (M2) has a value (M1 1):(M2 1) of from 400:1 to 600:1.

15. The method according to claim 1, wherein the cosmetic agent (M1) and the cosmetic agent (M2) have identical pH values.

16. The method according to claim 1, wherein the cosmetic agent (M2) includes at least one oxidizing agent (M2-2) selected from the group consisting of persulfates, peroxodisulfates, chlorites, hypochlorites, hydrogen peroxide and the solid addition products thereof with urea, melamine, polyvinylpyrrolidone and sodium borate, in a total amount of from 0.5 to 10% by weight based on the total weight of the cosmetic agent (M2).

* * * * *